United States Patent
Lied et al.

(10) Patent No.: US 10,213,473 B2
(45) Date of Patent: Feb. 26, 2019

(54) MARINE PEPTIDES AND NUCLEOTIDES

(71) Applicant: Firmenich SA, Geneva (CH)

(72) Inventors: Einar Lied, Bergen (NO); Oddvar Bjorge, Ellingsoy (NO)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/329,953

(22) PCT Filed: Jul. 30, 2015

(86) PCT No.: PCT/EP2015/067451
§ 371 (c)(1),
(2) Date: Jan. 27, 2017

(87) PCT Pub. No.: WO2016/016350
PCT Pub. Date: Feb. 4, 2016

(65) Prior Publication Data
US 2017/0258866 A1    Sep. 14, 2017

Related U.S. Application Data

(60) Provisional application No. 62/031,855, filed on Jul. 31, 2014.

(51) Int. Cl.
| | | |
|---|---|---|
| *A61K 38/00* | (2006.01) | |
| *A61K 38/01* | (2006.01) | |
| *A61K 35/60* | (2006.01) | |
| *A61K 35/612* | (2015.01) | |
| *A61K 36/02* | (2006.01) | |
| *A23L 33/18* | (2016.01) | |
| *A23L 17/20* | (2016.01) | |
| *A23L 33/00* | (2016.01) | |
| *A23L 33/13* | (2016.01) | |

(52) U.S. Cl.
CPC ............ *A61K 38/012* (2013.01); *A23L 17/20* (2016.08); *A23L 33/13* (2016.08); *A23L 33/18* (2016.08); *A23L 33/30* (2016.08); *A23L 33/40* (2016.08); *A61K 35/60* (2013.01); *A61K 35/612* (2013.01); *A61K 36/02* (2013.01); *A61K 38/011* (2013.01); *A23V 2002/00* (2013.01)

(58) Field of Classification Search
None
See application file for complete search history.

(56) References Cited

U.S. PATENT DOCUMENTS

2011/0039768 A1 *  2/2011  Drieu La Rochelle ... A23J 3/04
                                                        514/4.9

FOREIGN PATENT DOCUMENTS

| NO | 320667 | 8/2009 |
|---|---|---|
| WO | WO2003026682 A1 * | 4/2003 |
| WO | WO2006026682 | 3/2006 |

OTHER PUBLICATIONS

International Search Report and Written Opinion, application PCT/EP2015/067451 dated Sep. 4, 2015.
Abete et al., Nutrition, Metabol. & Cardio. Diseases (2011) 21, B1-B15.
Vikoren et al., British Journal of Nutrition (2013), 109, 648-657.

* cited by examiner

*Primary Examiner* — Jeanette M Lieb

(57) ABSTRACT

Provided herein is a method of reducing postprandial concentrations of glucose in a subject's blood comprising administering to the subject, prior to or during a meal, an effective amount of a combination of a marine peptide and a fish nucleotide, sufficient to reduce the glucose concentration in the subject's blood. Further provided herein is a method of reducing postprandial concentration of ghrelin in a subject's blood, comprising administering to the subject, prior to or during a meal, an effective amount of a combination of a marine peptide and a fish nucleotide sufficient to increase the blood component wherein the combination is administered to the subject.

14 Claims, No Drawings

MARINE PEPTIDES AND NUCLEOTIDES

This application is a 371 filing of International Patent Application PCT/EP2015/067451 filed 30 Jul. 2015, which claims the benefit of U.S. patent application No. 62/031,855 filed Jul. 31, 2014.

FIELD

Provided herein are fish products and by-products and their use in health, food, nutrition and medical treatment.

BACKGROUND

Postprandial blood glucose (or glycaemia), together with related hyperinsulinemia and lipidaemia, has been implicated in the development of chronic metabolic diseases like obesity, type 2 diabetes mellitus and cardiovascular disease. There is evidence linking postprandial glycaemia or glycaemic variability to the development of these conditions or in the impairment in cognitive and exercise performance.

Data show that protein ingestion before a meal, when consumed with carbohydrate, reduces postprandial blood glucose; the blood sugar lowering effects have in particular been linked to dairy proteins such as whey proteins. A recent study comparing whey protein with whey protein hydrolysate showed that whey protein consumed before a meal reduces food intake, postprandial blood glucose and insulin, and the ratio of cumulative blood glucose to insulin area under the curves (AUCs) in a dose-dependent manner. In contrast whey protein hydrolysate did not contribute to blood glucose control neither by insulin-dependent nor insulin-independent mechanisms.

Scientific data also indicates that marine proteins have potential as functional food ingredients addressing several of the current health issues related to metabolic syndrome including persistent elevated blood sugar and diabetes-2, fat and protein anabolism and catabolism in relation to body composition management and to natural age dependent muscle wasting (sarcopenia).

Studies have also shown that marine peptide in combination with marine nucleotides may lower inflammation and stimulate gastrointestinal function.

SUMMARY

Provided herein is a method of reducing postprandial concentrations of glucose in a subject's blood comprising administering to the subject, prior to or during a meal, an effective amount of a combination of a marine peptide and a fish nucleotide, sufficient to reduce the glucose concentration in the subject's blood.

Further provided is the use of a combination of a marine peptide and a fish nucleotide to reduce the postprandial concentration of glucose in a subject's blood comprising administering to the subject prior to or during a meal an effective amount of the combination.

Also provided herein is a composition comprising a combination of isolated marine peptide and isolated fish nucleotides in a ratio of about 10:1 by weight of the total weight of the combination.

Further provided is a method of increasing the Glucagon Like Protein-1 (GLP-1) level in a subject's blood comprising administering to the subject in need of having its GLP-1 levels reduced an effective amount of a marine peptide wherein the marine peptide is administered in the substantial absence of a marine nucleotide. Particularly, the marine peptide is administered to the subject prior to or during a meal.

Further provided herein is a method of reducing postprandial concentrations of ghrelin levels in a subject's blood comprising administering to the subject in need of having its ghrelin levels an effective amount of a marine peptide wherein the marine peptide is administered in the substantial absence of a marine nucleotide. Particularly, the marine peptide is administered to the subject prior to or during a meal.

Further provided herein is a method of providing a feeling of satiety to a subject comprising administering to the subject in need thereof about 20 to about 25 mg per Kg of body weight of a subject a marine peptide wherein the marine peptide is provided in the substantial absence of a marine nucleotide.

DETAILED DESCRIPTION

For the descriptions herein and the appended claims, the singular forms "a", "an" and "the" include plural referents unless the context clearly indicates otherwise. Thus, for example, reference to "a compound" refers to more than one compound. Also, the use of "or" means "and/or" unless stated otherwise. Similarly, "comprise," "comprises," "comprising" "include," "includes," and "including" are interchangeable and not intended to be limiting.

Provided herein also is an embodiment comprising a method of reducing postprandial concentrations of glucose in a subject's blood comprising administering to the subject an effective amount of a combination of a marine peptide and a fish nucleotide sufficient to reduce the glucose concentration in the subject's blood wherein the combination is administered to the subject prior to or during a meal.

In one embodiment the subject is an animal, more particularly a mammal.

In one embodiment, the subject is a human.

In one embodiment the subject is in need of glucose reduction.

In one embodiment, the GLP-1 levels in a subject's blood are raised, particularly where the subject is in need of such increase.

In one embodiment, a method is provided comprising administering an effective amount of a combination of a marine peptide and a fish nucleotide to a subject having an HbA1C (glycated hemoglobin) level equal to or greater than 6 for a period of time sufficient to reduce the HbA1C level, particularly where the HbA1C level is greater than 6.5, more particularly wherein the HbA1C level is greater than 7.

In one embodiment, a method is provided comprising administering an effective amount of a combination of a marine peptide and a fish nucleotide to a subject for a period of time sufficient to reduce the subject's insulin resistance, particularly where the subject is in need of such reduction.

In one embodiment, provided herein is a method for managing the glucose levels in a subject.

In one embodiment a pharmaceutical preparation is provided comprising a combination of a marine peptide and a fish nucleotide in an amount sufficient for the treatment, to a subject in need of such treatment, of a condition selected from the group consisting of pre-diabetes, diabetes or obesity.

In one embodiment a dietary supplement is provided comprising a combination of a marine peptide and a fish nucleotide in an amount sufficient for the maintenance, in a subject, of blood sugar health and/or weight health.

In one embodiment a food, more particularly a functional food, is provided comprising a combination of a marine peptide and a fish nucleotide in an amount sufficient for the maintenance, in a subject, of blood sugar health.

In one embodiment a food, more particularly a functional food, is provided comprising a combination of a marine peptide and a fish nucleotide in an amount sufficient for the maintenance, in a subject, of glucose blood levels.

In one embodiment a method is provided comprising administering a food, more particularly a functional food, comprising a combination of a marine peptide and a fish nucleotide in an amount effective to manage of glucose levels in a subject.

Further provided is a method of increasing the Glucagon Like Protein-1 (GLP-1) level in a subject's blood comprising administering to the subject in need of having its GLP-1 levels reduced an effective amount of a marine peptide wherein the marine peptide is administered in the substantial absence of a marine nucleotide. Particularly, the marine peptide is administered to the subject prior to or during a meal.

Further provided herein is a method of reducing postprandial concentrations of ghrelin levels in a subject's blood comprising administering to the subject in need of having its ghrelin levels an effective amount of a marine peptide wherein the marine peptide is administered in the substantial absence of a marine nucleotide. Particularly, the marine peptide is administered to the subject prior to or during a meal.

In one embodiment provided herein is a method of increasing postprandial concentrations of GLP-1 levels in a subject's blood comprising administering to the subject in need thereof a about 20 mg to 25 mg per Kg of the body weight of the subject. Particularly, the marine peptide is administered to the subject prior to or during a meal.

In one embodiment provided herein is a method of reducing postprandial concentrations of ghrelin levels in a subject's blood comprising administering to the subject in need of having its ghrelin levels reduced about 20 mg to about 25 mg per Kg of the body weight of the subject. Particularly, the marine peptide is administered to the subject prior to or during a meal.

In one embodiment, provided herein is a method of providing a feeling of satiety to a subject comprising administering to the subject in need thereof, about 20 to about 25 mg per Kg of body weight of the subject. Particularly, the marine peptide is administered for a time sufficient to provide a feeling of satiety to the subject. In a further embodiment, the method to provide a feeling of satiety in a subject is provided in the substantial absence of a marine nucleotide, particularly less than 10%, more particularly less than 5%, more particularly less than 1%, more particularly less than 0.1%, even more particularly no marine nucleotide.

In one embodiment a dietary supplement is provided comprising a marine peptide in an amount sufficient for the maintenance, in a subject, of GLP-1 health wherein the supplement is provided in the substantial absence of a marine nucleotide. In one embodiment, a dietary supplement is provided comprising a marine peptide in amount sufficient for the maintenance, in a subject, of ghrelin health wherein the supplement is provided in the substantial absence of a marine nucleotide.

In one embodiment a food, more particularly a functional food, is provided comprising a marine peptide in an amount sufficient for the maintenance, in a subject, of GLP-1 levels wherein the food, more particularly a functional food, is provided in the substantial absence of a marine nucleotide.

In one embodiment a food, more particularly a functional food, is provided comprising a marine peptide in an amount sufficient for the maintenance, in a subject, of ghrelin blood levels.

In a particular embodiment, the maintenance of GLP-1 levels and health and/or ghrelin levels or health includes the management of hunger, satiety, body weight and/or obesity in a subject. Particularly, the management of GLP-1 levels and/or ghrelin levels provides for the maintenance of a healthy body.

In one embodiment a pharmaceutical preparation is provided comprising a marine peptide in an amount sufficient for the treatment of obesity.

Further provided is the use of a combination of a marine peptide and a fish nucleotide as described herein.

In one embodiment, the marine peptide is provided, when used in combination with a marine nucleotide, in an amount of from about 5 mg to about 50 mg per 1 Kg bodyweight of a subject, particularly about 5 mg to about 40 mg per Kg bodyweight, more particularly about 10 mg to about 30 mg per Kg bodyweight and even more particularly about 20 mg per Kg bodyweight of the subject. In a more particular embodiment the marine peptide, when used in combination with a marine nucleotide is provided in an amount of about 10 mg per Kg bodyweight of the subject. In yet another embodiment, the marine peptide, when provided in combination with a marine nucleotide, is provided in an amount of about 25 mg per Kg bodyweight of the subject.

In one embodiment, the marine nucleotide is provided in an amount of from about 0.8 to about 8 mg per Kg bodyweight of a subject, particularly about 0.8 mg to about 6 mg per Kg body weight, more particularly about 2 to about 6 per Kg bodyweight and even more particularly about 4 mg per Kg bodyweight of the subject. In a more particularly embodiment the marine nucleotide is provided in an amount of about 2 mg per Kg bodyweight of the subject. In a further embodiment, the marine nucleotide is provided in an amount of about 3 mg per Kg bodyweight of the subject.

In one embodiment, a method is provided comprising administering a marine peptide in a unit dose in, at least, an amount selected from the group consisting of 25 mg, 50 mg, 75 mg, 100 mg, 125 mg, 150 mg, 175 mg, 200 mg, 225 mg, 250 mg, 275 mg, 300 mg, 325 mg, 350 mg, 400 mg, 425 mg, 450 mg, 475 mg, 500 mg, 1000 mg, 1500 mg 2000 mg, 2500 mg and 3000 mg. In a particular embodiment, the unit dose comprises a fish nucleotide in an amount of about 10% of the weight of the marine peptide, particularly about 15% of the weight of the marine peptide, more particularly about 20% of the weight of the marine peptide and even more particularly about 25% of the weight of the marine peptide.

In one embodiment, the marine peptide is part of a food, more particularly a functional food, formulation where the quantity of marine peptides per serving is 200 mg-2500 mg.

In one embodiment, marine peptide and marine nucleotide, particularly the Sodium DNA can be present in ratio of 1:4 to 1:10 per serving of food, more particularly a functional food. The level of marine nucleotides can vary from 20 to 250 mg. In one embodiment, a method is provided comprising administering a marine nucleotide in a unit dose in, at least, an amount selected from the group consisting of 3 mg, 5 mg, 7.5 mg, 10 mg, 13 mg, 15 mg, 18 mg, 20 mg, 23 mg, 25 mg, 28 mg, 30 mg, 33 mg, 35 mg, 40 mg, 44 mg, 45 mg, 48 mg, 50 mg, 100 mg, 150 mg 200 mg, 250 mg and 300 mg. In a particular embodiment, the unit dose comprises a fish nucleotide in an amount of about 10% of the weight of the marine peptide, particularly about 15% of the weight of the marine peptide, more particularly about 20% of the weight of the marine peptide and even more particularly about 25% of the weight of the marine peptide.

In a further embodiment provided herein is a composition comprising a combination of isolated marine peptide and isolated fish nucleotides in a ratio of about 10:1 to about 2:1, particularly from about 6.4:1 to about 4:1, more particularly at about 4:1 (the ratio of the marine peptides to fish nucleotides) by weight of the total weight of the combination.

Also provided herein is use of a marine peptide and a fish nucleotide to reduce postprandial concentrations of glucose in a subject's blood comprising administering to the subject an effective amount of a combination of a marine peptide and a fish nucleotide sufficient to reduce the glucose concentration in the subject's blood.

Marine peptides may be obtained for example, but not limited to fish, marine algae, crustaceans and shellfish. Provided herein is marine peptide selected from the group consisting of fish, marine algae, crustaceans, and shellfish. In a particular embodiment, the marine peptide is a fish peptide. Isolated herein means for, marine peptide, marine protein hydrolysates generally processed from the marine source more particularly from fish. Isolated herein means, for fish nucleotides, fish DNA or fragments thereof and physiologically acceptable salts thereof, particularly a sodium salt. In one particular embodiment, isolated fish nucleotides comprise DNA extracted from fish soft roe. See for example Norwegian Patent Number 20014670. In a particular embodiment, the fish nucleotides comprise essentially pure DNA or fragments thereof, particularly fish nucleotides having less than 2% protein. Isolated is not meant to limit the ability in practicing embodiments herein to combine the isolated ingredients for example with fish or fish products in the preparation of a pharmaceutical product, a dietary supplement or a food, more particularly a functional food.

In one embodiment, provided herein is a process for making marine peptides comprising:
a) mixing marine raw materials with water an and enzyme to form a marine material mixture; particularly an enzyme selected from endopeptidases;
b) homogenizing the marine material mixture to form a homogenate;
c) heating the homogenate for a time period of up to about 45 minutes to form an incubate;
d) deactivating the enzyme to form an incubate with deactivated enzymes;
e) optionally separating the bones from the incubate to form an incubate having a water soluble protein rich fraction;
f) Separating the water soluble and peptide rich fraction from the incubate to obtain a hydrolysate peptide product;
g) optionally filtering or ultrafiltering the hydrolysate to remove micro-particles; and
h) optionally spray drying the hydrolysate to form a free-flowing powder.

In one embodiment, the isolated marine peptide here means marine peptides wherein at least 70%, particularly, at least 75% and more particularly at least 85% of the peptides have a molecular weight of less 5000 Dalton (Da). In another embodiment, 90% of the peptides have a molecular weight of less than 10000 (2) Da. In one embodiment the marine peptide comprises a water free protein content of about 95%. In a particular embodiment the marine peptide has the peptide molecular weight profile as set forth in (Profile I):

| Peptide (Molecular Weight (Da) | Amount (Dried Weight Bases) |
| --- | --- |
| >20 KDa | 0-5%. |
| 15 KDa-20 KDa | 0-5% |
| 10 KDa-15 KDa | 0-5% |
| 8 KDa-10 KDa | 0-5% |
| 6 KDa-8 KDa | 0-5% |
| 4 KDa-6 KDa | 0-10% |
| 2 KDa-4 KDa | 0-15% |
| 1 KDa-2 KDa | 0-50% |
| 0.5 KDa-1 KDa | 0-50% |
| 0.2 KDa-0.5 KDa | 0-75% |
| <0.2 KDa | 0-75%. |

The total amount of the peptides is 100% (dried weight basis).

In one embodiment, the Molecular Weight Range of the peptides (KDa)—are, each independently, on a dried weight basis as follows (Profile 2):

| Peptide (Molecular Weight) | Amount (Dried Weight Basis) |
| --- | --- |
| >20 KDa | at about <0.1% |
| 15 KDa-20 KDa | at about <0.1 |
| 10 KDa-15 KDa | at about <0.1 |
| 8 KDa-10 KDa | at about 0.1 |
| 6 KDa-8 KDa | at about 0.5% |
| 4 KDa-6 KDa | at about 1.9 |
| 2 KDa-4 KDa | at about 6.3 |
| 1 KDa-2 KDa | at about 13.0 |
| 0.5 KDa-1 KDa | at about 18.5 |
| 0.2 KDa-0.5 KDa | at about 23.8 |
| <0.2 KDa | at about 24.0 |
| Free AA | 0-20%, particularly at about 3.5 |
| EAA/NEAA ratio | 0.4-0.9, particularly at about 0.7 |

In one embodiment, the sum of the branched chain amino acid is greater than or equal to about 15.31% on a total amino acids basis.

In one embodiment, the indispensable amino acids or essential amino acids are about 36.70% of the total amino acids.

In one embodiment, the marine peptide is as described in Norwegian Patent Number 20040450.

The process for making marine peptides typically begins with fresh or fresh frozen fish muscle tissue which is minced and mixed with water at a ratio 1:1 in an incubator (e.g., but not limited to a 1-20 $m^3$ volume incubator). The temperature is raised to 50-55° C. while the mixture stirred preferably at 50-80 rpm. An enzyme cocktail consisting of a mixture of proteases and peptidases is added (e.g., Protamex® from NOVOZYMES, Denmark) to the mixture and the temperature is brought to about 50 to 55° C. and the homogenate formed is incubated for 45 min at 50-55° C. at pH 6-8, preferably at 6-7. Then the temperature is raised to 85-90° C. and kept at that temperature for about 10-15 min to inactivate the enzymes. The incubate is passed through a sieve to remove bones and debris, then the soluble fraction is separated from the indigestible/insoluble material using centrifugation after which the peptide rich soluble fraction is dehydrated into a concentrate, which is used for spray-drying into a powder.

The amino acid profile of the marine peptides made as set out above is provided in Table 1.

TABLE 1

Amino acid profile in terms of dry matter

| Amino acids | Total amino acid (mg/g) | Free amino acids (mg/g) | Percent (%) of total amino acids |
|---|---|---|---|
| Indispensible IDAA | | | |
| Histidine | 13.5 | 0.26 | 1.93 |
| Threonine | 30.9 | 1.20 | 3.88 |
| Methionine | 22.1 | 2.30 | 10.41 |
| Phenylalanine | 23.2 | 2.75 | 11.85 |
| Valine | 36.9 | 1.94 | 5.26 |
| Isoleucine | 30.1 | 1.91 | 6.35 |
| Leucine | 60.3 | 6.35 | 10.53 |
| Lysin | 71.3 | 1.36 | 1.91 |
| Tryptofan | 6.0 | 0.48 | 8.00 |
| Total IDAA | 367.0 | 18.55 | 5.05 |
| Sum BCAA | 153.1 | 10.21 | 6.66 |
| Dispensible DAA | | | |
| Aspartic acid | 73.32 | 1.18 | 1.49 |
| Asparagine | — | 0.38 | — |
| Glutamic acid | 125.0 | 5.30 | 4.24 |
| Glutamine | — | 0.78 | — |
| Hydroxyproline | 1.0 | 0.08 | 8.00 |
| Serine | 36.0 | 1.11 | 3.08 |
| Glycine | 50.9 | 1.22 | 2.40 |
| Alanine | 47.8 | 3.26 | 6.82 |
| Proline | 29.7 | 0.49 | 1.65 |
| Tyrosine | 22.7 | 1.43 | 6.30 |
| Arginine | 51.1 | 1.47 | 2.88 |
| Cystin | na | 0.01 | — |
| Total DAA | 521 | 16.96 | 3.25 |
| Taurin | 6.6 | 6.60 | 100 |
| Sum amino acids | 737.8 | 35.26 | 4.77 |
| | 0.70 | 1.09 | |

The chemical composition of the marine peptides made as described above is provided in Table 2.

TABLE 2

Chemical composition

| Proximal comp (%) | |
|---|---|
| Protein (N × 6.25) | >88.0 |
| Total fat | <0.2 |
| Carbohydrates | 0 |
| Water | <3.0 |
| Ash | 10.0 |
| Minerals (%) | |
| Salt (NaCl) | 0.1 |
| Sodium | 1.7 |
| Chloride | 0.07 |
| Heavy metals (ppm) | |
| Lead | 0.1 |
| Cadmium | 0.03 |
| Mercury | 0.11 |
| Arsen | 49.0 |

Arsen present as organic bound and non-toxic.

The microbiological profile of the marine peptides made as described above is provided in Table 3.

| Microbiology (per gram powder) | |
|---|---|
| Total count (30 dgr C.) | 100 |
| Enterobacteriace (37 dgr C.) | 0 |
| E. coli (44.5 dgr C.) | 0 |
| Staphylococcus. coagulase pos | 0 |
| ASR-Clostridium (37 dgr C.) | 50 |
| ASR-Clostridium (37 dgr C.) - 2 days | 50 |
| Salmonella spp | Neg/25 g |
| Listeria monocytogenes | 0 |
| Mould | <10 |
| Yeast | <10 |

The molecular weight distribution of the marine peptide hydrolysate of the marine peptides made as set forth above is provided in Table 4.

TABLE 4

Molecular weight distribution of marine protein hydrolysate

| Molecular weight Distribution | Amino acid moieties | g/100 g soluble peptides | g/100 g dry matter |
|---|---|---|---|
| Chromatography | | | |
| >20.000 Da | | <0.1 | 0 |
| 20.000-15.000 Da | | <0.1 | 0 |
| 15.000-10.000 Da | | <0.1 | 0 |
| 10.000-8.000 Da | 88-71 | 0.1 | 0.09 |
| 8.000-6.000 Da | 70-53 | 0.6 | 0.54 |
| 6.000-4.000 Da | 52-36 | 2.1 | 1.89 |
| 4.000-2.000 Da | 35-18 | 7.2 | 6.48 |
| 2.000-1.000 Da | 17-10 | 14.8 | 13.32 |
| 1.000-500 Da | 9-5 | 21.0 | 18.90 |
| 500-200 Da | 4-2 | 27.0 | 24.30 |
| <200 Da | <2 | 27.2 | 24.48 |
| Calculated values | | | |
| Free amino acids | | 5.1 | 4.59 |
| Dipeptides | | | 19.89 |
| >10.000 Da | >88 | 0.1 | 0 |
| <10.000 Da | <88 | 99.9 | 90.0 |
| <2.000 Da | <17 | 90.0 | 81.0 |
| <1.000 Da | <9 | 75.2 | 67.7 |

The following was used for calculations for the results set forth in:
Average MW amino acid=132
Average MW amino acid when present in a peptide=113.5
Smallest possible dipeptide present=Glycyl-Glycine=MW 132
Largest possible dipeptide present=Tryptyl-Tryptophan=MW 390

Still in a further embodiment, provided herein is a unit dose having an effective amount of a marine peptide and a fish nucleotide.

In some embodiments, the marine peptide and/or fish nucleotide is administered in a single dosage form, i.e., a dosage form, or in two or more dosage forms. As used herein, "dosage form" refers to the physical form for the route of administration. The term "dosage form" can refer to any traditionally used or medically accepted administrative forms, such as oral administrative forms, intravenous administrative forms, or intraperitoneal administrative forms. In some embodiments, the marine peptide and/or fish nucleotide is administered in a single dose, i.e., a unit dose. As used herein, a "unit dose" refers to an amount of marine peptide and/or fish nucleotide administered to a subject in a single dose, e.g., in a gel capsule. The term "unit dose" can also refer to a single dosage form of a single unit of a suitable solid, liquid, syrup, beverage, or food, more particularly a functional food, item, for example, but not limited to, those used to deliver pharmaceutical, dietary supplements and food, more particularly a functional food, wherein the total dose of marine peptide and/or fish nucleotide is administered within a short period of time, e.g., within about 1 minute, 2 minutes, 3 minutes, 5 minutes, 10 minutes, 20 minutes, or 30 minutes of a first portion of a dose. So for example if the dose form is a food, more particularly a functional food, it may be part of any food product with 200-2000 mg per serving of food, more particularly a functional food, where the serving is defined by the manufacturer/regulator based on the type of food, more particularly a functional food; for example it may be sprinkled onto the food and eaten with the meal with the above mentioned level per serving.

In one embodiment, the unit dose is delivered via a unit dosage form such as tablets, capsules, cachets, pellets, pills, gelatin capsules, powders, and granules. In a particularly embodiment provided herein is a capsule and or table that comprises about 500 mg of a marine peptide and about 50 mg of a marine nucleotide.

In one embodiment, about 1500 mg, more particularly about 2000 mg of a marine peptide is provided in a single dosage unit of a beverage. In one embodiment, about 150, more particularly about 200 mg of a marine nucleotide is provided in a single dosage unit of a beverage.

In some embodiments, the subject to be treated can be administered at least one unit dose per day. In some embodiments, the dosage forms can be taken in a single application or multiple applications per day. For example, if four capsules are taken daily, each capsule comprising about 500 mg marine peptide and/or fish nucleotide, then all four capsules could be taken once daily, or 2 capsules could be taken twice daily, or 1 capsule could be taken every 6 hours. Various amounts of marine peptide and/or fish nucleotide can be in a unit dose. In some embodiments, the unit dose comprises about 25 mg, 50 mg, 75 mg, 100 mg, 125 mg, 150 mg, 175 mg, 200 mg, 225 mg, 250 mg, 275 mg, 300 mg, 325 mg, 350 mg, 400 mg, 425 mg, 450 mg, 475 mg, 500 mg, 1000 mg, 1500 mg 2000 mg, 2500 mg and 3000 mg.

The term "administering" or "administration" of a composition herein refers to the application of the composition, e.g., oral or parenteral (e.g., transmucosal, intravenous, intramuscular, subcutaneous, rectal, intravaginal, or via inhalation) to the subject. Administering would also include the act of prescribing a composition described herein to a subject by a medical professional. Administering can also include the act of labeling a composition, i.e., instructing a subject to administer a composition, in a manner as provided herein for treatment. By way of example, administration may be by parenteral, subcutaneous, intravenous (bolus or infusion), intramuscular, or intraperitoneal routes. Dosage forms for these modes of administration may include conventional forms, either as liquid solutions or suspensions, solid forms suitable for solution or suspension in liquid prior to injection, or as emulsions.

In a particularly embodiment a route of administration is oral administration. In a particular embodiment the marine peptide and/or fish nucleotide is administered to individuals in the form of nutritional supplements, foods, pharmaceutical formulations, or beverages, particularly foods, beverages, or nutritional supplements, more particularly, foods and beverages, more particularly foods. A particular type of food is a functional or medical food (e.g., a food which is in a formulation to be consumed or administered externally under the supervision of a physician and which is intended for the specific dietary management of a disease or condition for which distinctive nutritional requirements, based on recognized scientific principles, are established by medical evaluation).

Dietary supplements is interchangeable with nutritional supplements and may include a food preparation.

The marine peptide and/or fish nucleotide can be formulated in a dosage form. These dosage forms can include, but are not limited to, tablets, capsules, cachets, pellets, pills, gelatin capsules, powders, and granules. Parental dosage forms which include, but are not limited to, solutions, suspensions, emulsions, coated particles, and dry powder comprising an effective amount of the marine peptide and/or fish nucleotide as taught in this invention. In some embodiments, the dosage form can be inserted or mixed into a food substance. Various substances are known in the art to coat particles, including cellulose derivatives, e.g., microcrystalline cellulose, methyl cellulose, carboxymethyl cellulose; polyalkylene glycol derivatives, e.g., polyethylene glycol; talc, starch, methacrylates, etc. In some embodiments, the dosage form is a capsule, wherein the capsule is filled with a solution, suspension, or emulsion comprising the marine peptide and/or fish nucleotide. It is also known in the art that the active ingredients can be contained in such formulations with pharmaceutically acceptable excipients such as diluents, fillers, disintegrants, binders, lubricants, surfactants, hydrophobic vehicles, water soluble vehicles, emulsifiers, buffers, humectants, moisturizers, solubilizers, preservatives, flavorants, taste-masking agents, sweeteners, and the like. Suitable excipients can include, e.g., vegetable oils (e.g., corn, soy, safflower, sunflower, or canola oil). In some embodiments, the preservative can be an antioxidant, e.g., sodium sulfite, potassium sulfite, metabisulfite, bisulfites, thiosulfates, thioglycerol, thiosorbitol, cysteine hydrochloride, alpha-tocopherol, and combinations thereof.

The examples provided below are not limiting and are for illustrative purposes only.

EXAMPLES

Example 1

A double blinded study comprising 12 healthy male test persons was performed with four (4) different diets as described below:

1. Diet A: (control diet) casein (30%)+plus carbohydrate (55% maltodextrins)+fat (11% medium chain triglyceride (MCT)); i.e. 30 g of protein from casein per 100 g of diet.
2. Diet B: control diet in which 10% of the casein is replaced by marine peptide (marine protein hydrolysate) in terms of crude protein (N×6.25); i.e. the protein fraction in the diet is composed of 3.2% of protein from marine peptides and 26.7% of protein from casein.
3. Diet C: control diet in which 10% of the casein is replaced by whey peptide (whey peptide hydrolysate) in terms of crude protein (N×6.25) i.e. 3.2 g of protein from whey peptide and 26.8 g of protein from casein.
4. Diet D: control diet in which 10% of the casein is replaced by marine peptide (marine protein hydrolysate) in terms of crude protein (N×6.25); i.e. the protein fraction in the diet is composed of 3.2% (3.2 g per 100 g of Diet) of protein from marine peptides and 26.7% of protein from case plus supplementation of 0.5% (0.5 g per 100 g diet) of nucleotides from marine DNA (fish soft roe powder. No adjustments in dietary nitrogen were made due to the small amount of DNA added.

Test subjects were instructed to rest in bed after ingesting the test diet; blood samples were drawn no later than 5 min before ingesting the diets, and at 20 min intervals for 120 min following ingestion the test diets. The diets were taken within a period of 5 min.

The subjects took all diets ideally in a random order. Diet B, C and D were given in amounts equivalent to 20 mg of peptide/kg bodyweight/dose and compared to equal intake of control Diet A in terms of energy and protein.

All blood samples were analyzed for blood glucose and insulin. Samples collected at −5 min (i.e. 0 time), 60 and 100 min were be analyzed for the hormones GLP-1 and ghrelin. Samples for GLP-1 analysis were collected in tubes containing GLP-1 protease inhibitor as a stabilizer.

The diets were taken as fluid meals. A powder composed of casein, maltodextrins (DE 20-21) from corn, vegetable fat (MCT fat powder), and supplemented with either (1) fish protein hydrolysates made of fish fillet from Atlantic cod, (2) whey protein hydrolysates or (3) fish protein hydrolysates plus marine nucleotides in the form of sodium-DNA extracted from soft roe of Atlantic cod (*Gadus morhua*) was dissolved in water to form a creamy drink before ingestion. Mixing ratio: 1 g powder plus 4 ml cold water.

The dietary distribution of protein, fat and carbohydrate is 30, 11 and 55%, respectively; the energy content was 4.4 Kcal/gram dry matter. The diets were given a natural strawberry flavor to level out any taste differences between diets.

All diets were given
  in amounts equivalent to 20 mg of peptide/kg bodyweight, consequently the amount given was adjusted to the test person's body weight.
Day 1
  The Subjects were fasting and were not allowed to eat any breakfast before this visit and come to clinic in the morning. Vital sign and a pre-ingestion blood sample were taken. After the diet was ingested blood samplings were taken at the following time points: 20 min, 40 min, 60 min, 80 min, 100 min, and 120 min.
Day 3
  The Subjects were fasting and were instructed to not eat breakfast before this visit. A pre-ingestion blood sample was taken. After the diet was ingested blood was taken at the following time points: 20 min, 40 min, 60 min, 80 min, 100 min, and 120 min.
Day 5
  The Subjects were fasting and were instructed to not eat breakfast before this visit. A pre-ingestion blood sample was taken. After the diet has been ingested blood is taken at the following time points: 20 min, 40 min, 60 min, 80 min, 100 min, and 120 min.
Day 7
  The Subjects were fasting and were instructed to not eat breakfast before this visit. A pre-ingestion blood sample was taken. After the diet was ingested blood was taken at the following time points: 20 min, 40 min, 60 min, 80 min, 100 min, and 120 min.
Results The area under the curve is calculated by taking the average response of all 12 participants and using the sum of positive responses in terms of mmol glucose per L blood exceeding the baseline (0 on the y-axis in the figure) without including the negative values (i.e. values below the baseline representing the rebound effect of insulin) and the following results were obtained:
  1. Control diet: 5.2 mmol/L
  2. Whey Peptide diet: 5.2 mmol/L
  3. Marine Peptide diet: 4.6 mmol/L
  4. Marine Peptide+Marine Nucleotides diet: 4.2 mmol/L
Comparison between diets:

1. Control diet vs Whey peptide diet: No difference
  2. Control diet vs Marine Peptide diet: 13% reduction in postprandial blood glucose response in favor of Marine Peptides
  3. Whey peptide diet vs Marine Peptide diet: 13% reduction in postprandial blood glucose response in favor of Marine Peptides
  4. Control diet vs Marine Peptide+Marine Nucleotide diet: 19% reduction in postprandial blood glucose response in favor of Marine Peptides+Marine Nucleotides.

It was also found that:

Marine Peptides lowered the postprandial blood glucose peak by 0.7 and 0.8 mmol/L, respectively, as compared to the Control and the Whey Peptide diets corresponding to 33 and 35%, respectively.

GLP and Ghrelin

The concentration of Ghrelin was measured at 4 different times following the ingestion of the diet; assuming a Ghrelin negative peak at 60 min postprandialy the analysis showed:
  1. Control diet: −14.3 ng/L
  2. Whey Peptide (WPH) diet: −21.2 ng/L
  3. Marine Peptide diet: −26.6 ng/L
  4. Marine Peptide+Marine Nucleotides diet: −3.5 ng/L The concentration of Ghrelin is inversely related to the feeling of hunger, consequently the lower the concentration of ghrelin in blood the stronger is the feeling of satiety. The data shows that marine peptides strongly affect the secretion of Ghrelin, and is assumed to also affect the feeling of satiety. The result for the marine peptide alone was shown to be higher than for whey peptide. The combination of marine peptide and marine nucleotide did not show a response.

The concentration of GLP-1 was measured at four different times following the ingestion of the test diet; assuming a GLP-1 peak at 60 min postprandialy the analysis showed:
  1. Control diet 0.76 ng/i
  2. Whey Peptide (WPH) diet: 0.28 ng/L
  3. Marine Peptide diet: 0.99 ng/L
  4. Marine Peptide+Marine Nucleotides diet: 0.61 ng/L GLP-1 has a variety of functions in the body, among them participating in the management of hunger and safety. Increased GLP-1 concentration of the blood lowers the feeling of hunger and prolongs the feeling of satiety.

The data shows that marine peptide supplementation affects the secretion of GLP-1, and superior to that of WPH. The stronger response of marine peptides on the GLP-secretion it is assumed will affect the feeling of satiety. Supplementation with a combination of marine peptides and marine nucleotides did not have any effect on the GLP-1 secretion.

The invention claimed is:

1. A method of reducing postprandial concentrations of glucose in a subject's blood comprising administering to the subject an effective amount of a combination of marine peptides and fish nucleotides sufficient to reduce the glucose concentration in the subject's blood, wherein the combination is administered to the subject prior to or during a meal; wherein the marine peptides and the fish nucleotides are present in a ratio of about 2:1 to about 10:1 by weight of the total weight of the combination; wherein the marine peptides are obtained by enzymatic hydrolysis of at least one marine protein and have a molecular weight in the range of from 1 to 20,000 Da; and wherein the fish nucleotides are extracted from tissue of fish, marine algae, crustaceans or shellfish and have less than 2% proteins comprising essentially of pure DNA or fragments thereof.

2. The method as recited in claim 1 wherein the subject is a human.

3. The method as recited in claim 1 wherein the subject is in need of such reduction.

4. The method as recited in claim 1 wherein the marine peptide is provided in an amount of about 5 mg to about 50 mg per 1 Kg bodyweight of the subject.

5. The method as recited in claim 4 wherein the marine peptide is provided in an amount of about 20 mg per Kg bodyweight of the subject.

6. The method as recited in claim 1 wherein the combination is administered to the subject for a period of time sufficient to reduce the subject's insulin resistance.

7. The method as recited in claim 1 wherein the combination is administered to a subject having an HbA1C level equal to or greater than 6 for a period of time to reduce the HbA1C level.

8. The method as recited in claim 7 wherein the HbA1C level is greater than 6.5.

9. The method as recited in claim 8 wherein the HbA1C level is greater than 7.

10. The method as recited according to claim 1 wherein the combination is provided as a fixed dietary for the management of glucose levels in the subject.

11. The method as recited according to claim 1 wherein the combination is provided as a pharmaceutical preparation for the treatment of a condition selected from the group consisting of pre-diabetes or diabetes.

12. The method as recited in claim 1 wherein the combination is provided in a dietary supplement for the maintenance of blood sugar health.

13. The method as recited in claim 1 wherein the fish nucleotide is provided in an amount equal to about 25% of the weight of the marine peptide.

14. A composition comprising a combination of isolated marine peptides and isolated fish nucleotides in a ratio of about 10:1 by weight of the total weight of the combination wherein the combination is provided in an amount effective to reduce blood levels of glucose in a subject; wherein the marine peptides are obtained by enzymatic hydrolysis of at least one marine protein and have a molecular weight in the range of from 1 to 20,000 Da; and wherein the fish nucleotides are extracted from tissue of fish, marine algae, crustaceans or shellfish and have less than 2% proteins comprising essentially of pure DNA or fragments thereof.

* * * * *